US00PP14037P39

(12) United States Plant Patent
Bessho

(10) Patent No.: US PP14,037 P3
(45) Date of Patent: Jul. 29, 2003

(54) PETUNIA PLANT NAMED 'KAKEGAWA S36'

(75) Inventor: Masao Bessho, Kakegawa (JP)

(73) Assignee: Sakata Seed Corporation, Yokohama (JP)

( * ) Notice: Subject to any disclaimer, the term of this patent is extended or adjusted under 35 U.S.C. 154(b) by 0 days.

(21) Appl. No.: 09/990,370

(22) Filed: Nov. 23, 2001

(65) Prior Publication Data

US 2003/0101498 P1 May 29, 2003

(51) Int. Cl.[7] ..... A01H 5/00
(52) U.S. Cl. ..... Plt./356
(58) Field of Search ..... Plt./356

(56) References Cited

U.S. PATENT DOCUMENTS

PP8,915 P * 9/1994 Danziger ..... Plt./356

OTHER PUBLICATIONS

UPOV–ROM GTITM Computer, Database, 2002/03, GTI Jouve Retrieval Software, citation for 'Kakegawa S36'.*

* cited by examiner

*Primary Examiner*—Bruce R. Campell
*Assistant Examiner*—Susan B. McCormick
(74) *Attorney, Agent, or Firm*—Jondle & Associates PC

(57) ABSTRACT

A Petunia plant particularly distinguished by its magenta flower color and creeping, mounding habit.

1 Drawing Sheet

Genus and species: Petunia hybrida.
Variety denomination: 'Kakegawa S36'.

BACKGROUND OF THE NEW PLANT

The present invention comprises a new and distinct cultivar of Petunia, botanically known as Petunia hybrida, and hereinafter referred to by the cultivar name 'Kakegawa S36'. 'Kakegawa S36' originated from a hybridization made in 1995 in Kakegawa, Japan. The male parent was a breeding line named P-1a (not patented). The female parent of 'Kakegawa S36' was a dwarf multiflora breeding line with cherry colored flowers named 88S-1318-1a-1a-1 (not patented). $F_1$ seed was obtained from this cross in 1995.

$F_1$ plants were grown in Kakegawa, Japan and evaluated during the spring of 1996. Segregation of plant and flower characteristics was observed due to segregation in the parent lines. $F_1$ plants were transplanted to a field in Salinas, Calif. during the summer of 1998. Two lines were selected and vegetatively propagated for further evaluation. The two lines were propagated again in 1999, and evaluated for fixed characteristics and ease of propagation. Final selection of one line from the two was made during the summer of 1999. The line was established as 'Kakegawa S36', and determined to have its characteristics firmly fixed.

'Kakegawa S36' has been found to retain its distinctive characteristics after two years and four cycles of vegetative propagation and this novelty is firmly fixed. The variety has demonstrated stability during this time and has no inherent variation or off-types.

DESCRIPTION OF PHOTOGRAPH

This new Petunia plant is illustrated by the accompanying photograph which shows blooms, and foliage of the plant in full color, the colors shown being as true as can be reasonably obtained by conventional photographic procedures.

DESCRIPTION OF THE NEW CULTIVAR

Figure 1:
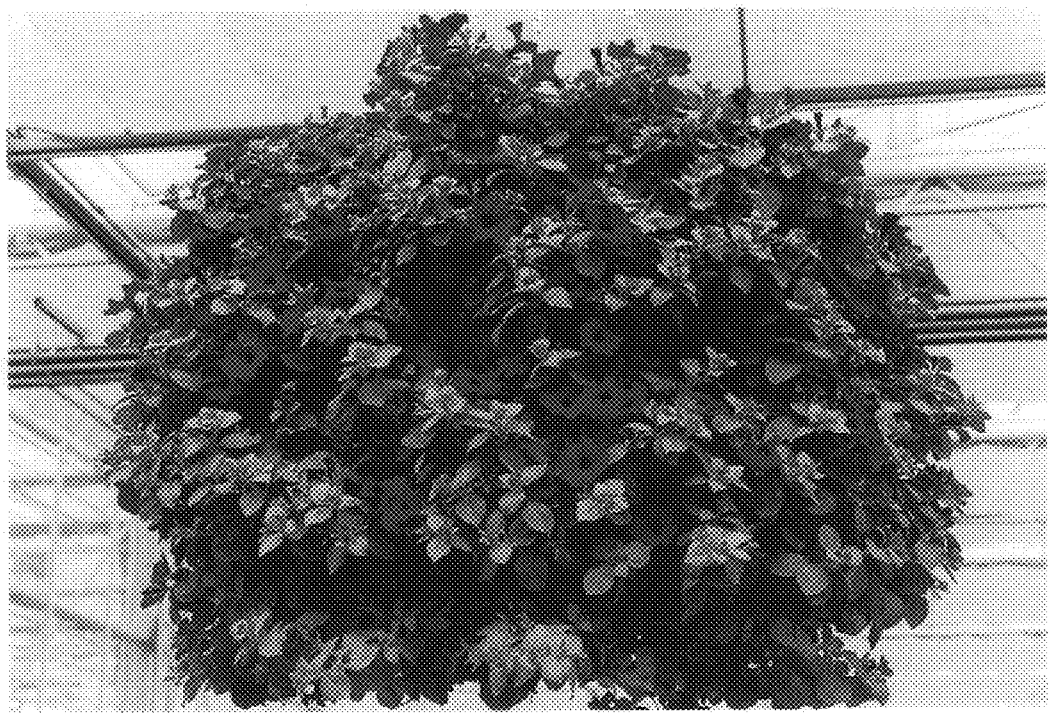
FIG. 1 shows the entire plant approximately eight weeks after transplanting a rooted cutting.
Figure 2:
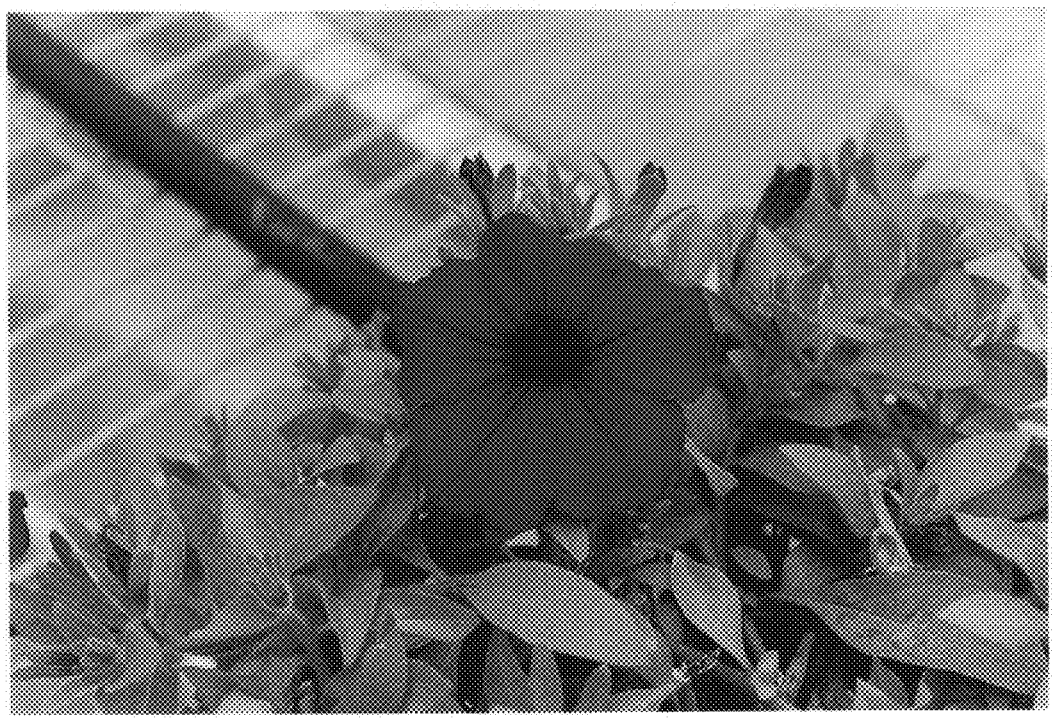
FIG. 2 shows the mature inflorescence.

The following detailed descriptions set forth the distinctive characteristics of 'Kakegawa S36'. The data which defines these characteristics were collected from asexual reproductions carried out in Salinas, Calif. Three plants from fully rooted 15 cm diameter pots were transplanted to one 50 cm diameter hanging baskets and grown in the same conditions. Data was collected on plants in 50 cm diameter pots eight weeks after rooted cuttings were transplanted. Color references are primarily to The R.H.S. Colour Chart of The Royal Horticultural Society of London (R.H.S.).

DESCRIPTION OF THE NEW PLANT

Classification:
- *Botanical.*—Petunia hybrida.
- *Commercial.*—Petunia.

Parentage:
- *Female parent.*—Breeding line 88S-1318-1a-1a-1 (not patented).
- *Male parent.*—Breeding line P-1a (not patented).

Environmental conditions for plant growth: Plants were propagated from vegetative cuttings, and grown individually in 15 cm diameter plastic pots in a glass greenhouse located in Salinas, Calif. Pots contained a peat moss-based growing medium. Soluble fertilizer containing 18% nitrogen, 8% phosphorus and 18% potassium was applied in four, daily irrigations. The fifth irrigation was made with non-fertilized water. Pots were top-dressed with a slow release fertilizer containing 18% nitrogen, 8% phosphorus and 18% potassium. The typical average air temperature was 24C.

Growth:
- *Habit.*—Branching, mounding.
- *Form.*—Descending.
- *Plant size.*—45 cm total diameter and 25 cm total height.
- *Flowering habit.*—Indeterminate.

*Time to initiate root development.*—7 days after sticking cuttings.
*Time to bloom from propagation.*—4–6 weeks after rooting when grown in 10–15 cm diameter plastic pots.
*Life cycle.*—Annual.

Stems:
*Color.*—Yellow-green (RHS 145A).
*Description.*—Round, pubescent.
*Diameter.*—2–3 mm.
*Internode length.*—4 cm.

Leaves:
*Arrangement.*—Opposite.
*Apex.*—Mucronate.
*Base.*—Oblique.
*Color.*—Upper surface is green (RHS 137B) and lower surface is green (RHS 138B).
*Margin.*—Entire.
*Size.*—Length is 4.8 cm and width is 2.5 cm, both at full expansion.
*Shape.*—Ovate.
*Texture.*—Coarse.
*Venation.*—Pinnate.
*Pubescence.*—Present, clear.

Buds:
*Bud color.*—Yellow-green (RHS 144C).
*Bud diameter.*—5.0 mm.
*Bud length.*—1.8 cm.

Flowers:
*Calyx.*—5 sepals; 2 cm×8 mm (length×width).
*Corolla.*—5 petals, fused.
*Flower diameter.*—7.0–7.5 cm.
*Fragrant.*—Yes.
*Inflorescence type.*—Solitary.
*Pistil.*—Compound.
*Ovary.*—Superior, parietal placentation.
*Stamens.*—5 total with two long and three short; purple (RHS 77B),
*Style.*—Purple (RHS 77A).
*Peduncle.*—2.7 cm×2 mm (length×width); pubescent.
*Petal color.*—Limbs: upper — red-purple (RHS N74A) with purple (RHS N78A) veins; lower — red-purple (RHS N74C) with purple (RHS N78A) veins. Tube: Inner — purple-violet (RHS N82A) with purple (RHS 79A) veins; Outside is purple-violet (RHS N82A) with purple (RHS 79A) veins.
*Petal margin.*—Smooth.
*Petal pubescence.*—Absent.
*Tube throat diameter.*—1.0 cm.
*Pollen color.*—Violet (RHS 85B).
*Produces seed.*—Yes; grey-orange (RHS 172B); <1.0 mm diameter; seed coat has netted pattern, 8–10,000 seeds/gram.

Disease and Insect Resistance

No susceptibility to diseases or insects noted to date.

Comparison with Known Cultivars

'Kakegawa S36' is a distinct variety of Petunia owing to its magenta flower color and creeping, mounding habit. 'Kakegawa S36' is most similar to the variety 'Purple Wave'; however, 'Kakegawa S36' has a magenta flower color. Table 1 below shows the characteristics that best distinguish the new variety from the comparison variety.

TABLE 1

| Characteristic | 'Kakegawa S36' | 'Purple Wave' |
|---|---|---|
| Flower diameter | 7.0–7.5 cm | 6.2–6.7 cm |
| Primary petal color (upper) | Magenta RHS 74A | Deep red-purple RHS 74A |
| Primary petal color (lower) | Magenta RHS 74C | Reddish purple RHS 72B |

Comparision with Parental Cultivars

TABLE 2

| Characteristic | 'Kakegawa S36' | P-1a (male) | 88S-1318-1a-1a-1 (female) |
|---|---|---|---|
| Plant Habit | Mounding | Creeping | Dwarf and compact |
| Flower Size | Grandiflora | Grandiflora | Grandiflora |
| Flower Petal Color | Magenta (RHS74A) | Magenta | Cherry |

I claim:

1. A new and distinct Petunia plant as shown and described herein.

* * * * *